United States Patent [19]
Schipper et al.

[11] Patent Number: 5,601,445
[45] Date of Patent: Feb. 11, 1997

[54] ELECTRICAL AND STRUCTURAL INTERCONNECTOR

[75] Inventors: Jeffery D. Schipper, Poway; David R. Williams, Temecula, both of Calif.

[73] Assignee: IMED Corporation, San Diego, Calif.

[21] Appl. No.: 403,502

[22] Filed: Mar. 13, 1995

[51] Int. Cl.⁶ .................................................... H01R 4/50
[52] U.S. Cl. ............................................................ 439/341
[58] Field of Search ................................. 439/341, 376, 439/660, 288, 293, 295; 604/66

[56] References Cited

U.S. PATENT DOCUMENTS

| | | |
|---|---|---|
| 1,482,833 | 2/1924 | Averill . |
| 2,253,971 | 8/1941 | Dodge ....................................... 439/341 |
| 2,369,860 | 2/1945 | Schroeder . |
| 3,969,796 | 7/1976 | Hodsdon et al. ......................... 24/270 |
| 4,316,304 | 2/1982 | Parise et al. ............................. 15/339 |
| 4,709,974 | 12/1987 | Hawkins ................................. 439/345 |
| 4,756,706 | 7/1988 | Kerns et al. ............................. 604/66 |
| 4,906,205 | 3/1990 | Viles ...................................... 439/504 |
| 5,133,680 | 7/1992 | Watson et al. .......................... 439/824 |
| 5,145,398 | 9/1992 | Manabe .................................. 439/341 |
| 5,249,979 | 10/1993 | Deinhardt et al. ...................... 439/341 |
| 5,302,136 | 4/1994 | St. Germain et al. .................. 439/376 |
| 5,306,174 | 4/1994 | Kiga ...................................... 439/341 |
| 5,398,162 | 3/1995 | Bice ...................................... 361/732 |
| 5,417,595 | 5/1995 | Cullen et al. .......................... 439/700 |

*Primary Examiner*—P. Austin Bradley
*Assistant Examiner*—Yong Kim
*Attorney, Agent, or Firm*—Pennie & Edmonds

[57] ABSTRACT

A connector for structurally and electronically interconnecting modular electronic components which permits as single connection to provide both electrical communication and structural support between the modular components is disclosed. The interconnector may be a separate component from the housing for the electronic components or may be integrated therein.

2 Claims, 3 Drawing Sheets

ELECTRICAL AND STRUCTURAL INTERCONNECTOR

BACKGROUND OF THE INVENTION

1. Technical Field

The present invention pertains generally to structural and electrical connectors. More specifically, the present invention pertains to a mechanism for interconnecting electronic components held in separate respective structural modules by structurally engaging the modules with each other while simultaneously providing for electrical communication between the components.

2. Discussion of Related Art

There are many applications in which it is necessary to structurally and electrically interconnect electronic components disposed within separate structural modules. Examples of such applications might include modular stereo components, portable communications equipment and electronics test equipment. Many other applications could be identified.

A more specific example of an application in which components must be electrically and structurally interconnected occurs in the provision of modern electronic medical patient care systems, such as those including intravenous (IV) fluid infusion to a patient.

One approach to providing an IV administration system that is responsive to modern varying and complex medical situations has been to create systems having separate components for performing different functions. A major benefit of such a system is that the system components can be selectively incorporated, as required, to meet the particular requirements for the system. For example, such a system is disclosed in U.S. Pat. No. 4,756,706 which issued to Kerns et al. for an invention entitled "Centrally Managed Modular Infusion Pump System". The problem with a modular system such as the one disclosed by Kerns, et al., however, is that as the medical situation becomes more complex and demanding, the set up and operation of the IV administration system also tends to become more complex. Again, by way of example, the device which Kerns et al. disclose in U.S. Pat. No. 4,756,706 requires the user to first structurally engage the modules, and subsequently, in a separate and distinct action, electrically interconnect the modular components.

The present invention recognizes that the complexity of setting up an IV administration system (or any analogous structural/electronic component system) can be significantly reduced by accomplishing the structural and electrical connections simultaneously in a single action. Other benefits such as reduced parts inventory and associated cost reductions can also result.

SUMMARY OF THE INVENTION

In light of the above it is an object of the present invention to provide a connector for both structurally engaging separate structural modules of an electronic system and for electrical communication therebetween.

Another object of the present invention is to provide an interconnector for structurally engaging separate components of such a system for electrical communication therebetween, wherein the structural and electrical connections between modules are accomplished simultaneously in an essentially one-step operation.

Yet another object of the present invention is to provide an easy to use, relatively simple to manufacture and comparatively cost effective device for structurally engaging separate structural components of an electronic system for electrical connections therebetween.

These and other objects are achieved according to the present invention by an electrical and structural interconnector which comprises first and second detachable parts. The first part has a body portion with an extending portion that extends in direction outward and upward from the body portion. At least one electrical conductor extends through the first part and terminates in a contact surface on the outer surface of the extending portion. The second part also has a body portion which defines a main body recess that is configured and dimensioned to slidingly receive the extending portion of the first part. The first part extending portion generally cannot be moved directly laterally or vertically into the second part main body recess. The first part extending portion is rotated upward and outward into the main body recess and thereby secures the parts together against lateral or vertical separation. There is also provided in the second part at least one electrical conductor that extends through the second part and terminates in a contact surface positioned within the main body recess. The contact surfaces of the first and second parts are placed together when the parts are attached to provide an electrical connection between the conductors. The specific configuration of the mating parts of the first and second parts allows either part to support the other in the vertical direction while at the same time resisting lateral separation.

In a further aspect of the invention, a modular system is provided with integral structural and electrical connectors. In this system, a first module has a wall formed to create a cavity. The wall provides an aperture for access into the cavity and there is a periphery around the aperture. A first electrical contact is positioned in the cavity of the first module. A second module also has a wall formed to create a cavity. An extension with an angled lip is mounted on the wall of the second module. The extension is dimensioned for insertion through the aperture in the wall of the first module and thus into the first module cavity in order to grip the periphery of the first module aperture. The periphery is gripped between the angled lip and wall of the second module upon rotation of the second module. A second electrical contact is embedded in the extension of the wall of the second module and placed to touch the first electrical contact in the cavity of the first module in order to establish electrical communication between the two modules. This arrangement also permits engagement and disengagement only upon appropriate rotation and allows either module to structurally support the other.

According to a further aspect of the invention, a multiplicity of modules may be interconnected in this same fashion.

DESCRIPTION OF THE PREFERRED EMBODIMENTS

Figure 1:
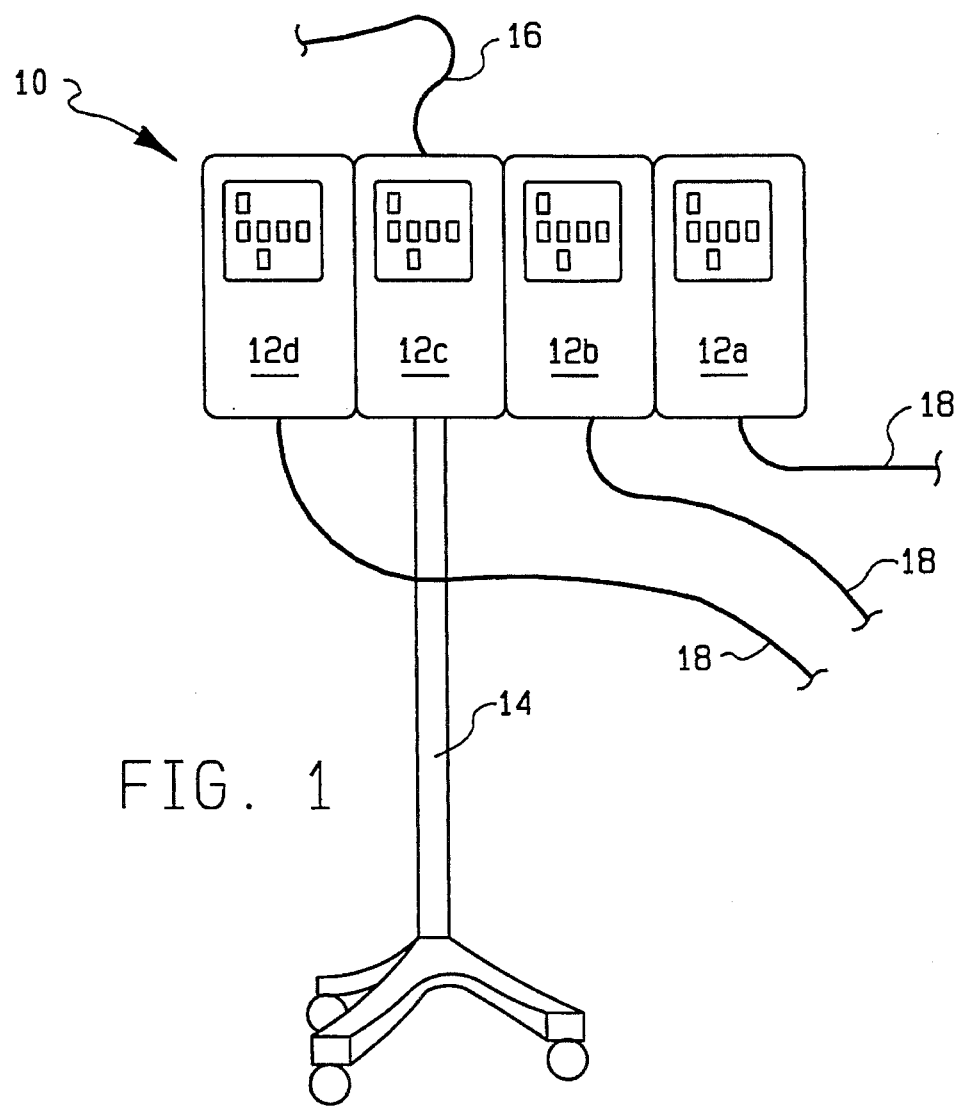
FIG. 1 is a front elevational view of a multi-module electronic system wherein the individual modules are interconnected structurally and electrically in accordance with the present invention.

Referring initially to FIG. 1, a multi-module system according to the present invention is shown and generally designated 10. By way of illustration, four structural modules 12a–d are shown interconnected and mounted on stand 14. It is to be appreciated, however, that more or fewer modules 12 may be incorporated into the system 10. Such a system may have one or more inputs 16 and one or more outputs 18.

For the purposes of the present invention, the specific function of each individual module is not critical. However, such modules are of a kind which each contain electronic components that must communicate either mono-directionally or bi-directionally for proper performance of their respective functions. Continuing with the illustrative example set forth above, one of the modules 12, for example, module 12c, may be a central control unit which monitors and/or controls the operations of various patient care modules 12a, 12b and 12d, such as large volume parenteral pumps, syringe pumps, pulse oximeters, EKG or other patient care devices. In this example, the present invention is capable of transferring electrical communication from one module to the next and also may be wired to provide direct communication between non-adjacent modules. The example of an IV administration system is one in which bi-directional communication between the modules may be required. An example of single-directional communication may be a modular stereo component system wherein the communication moves only outward, toward speaker modules.

However, for the purposes of the present invention, all of modules 12a, b, c and d may be considered alike in that each is provided with the same interconnector components according to the present invention, which allow them to be structurally and electrically interconnected in any order and at random with any other module to maintain the electrical and structural interconnection.

Figures 2, 3:
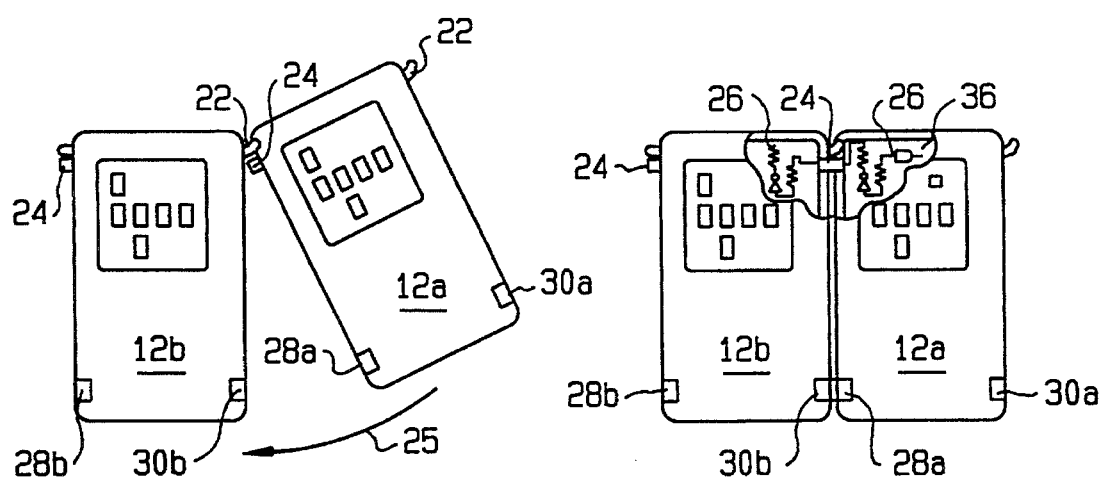
FIG. 2 is a front elevational view of a pair of modules positioned for subsequent engagement with each other.
FIG. 3 is a view of the modules shown in FIG. 2 after engagement and with portions broken away to reveal the interconnector according to the present invention and associated electronic components.

FIG. 2 shows two exemplary modules 12a and 12b in position for engagement. Specifically, male connector portion 22 of module 12b is placed for insertion into female connector portion 24 of module 12a. With a rotation of module 12a relative to module 12b in the direction of arrow 25 (or the opposite rotation of module 12b), the modules are engaged in a manner substantially as shown in FIG. 3. As shown in FIG. 3, upon structural engagement of modules 12a and 12b, electronic components 26 of module 12a are also electrically connected to electronic components 26 of module 12b. The exact manner by which these structural and electrical connections are simultaneously accomplished is discussed in detail below in conjunction with FIG. 4.

Still referring to FIG. 3, it will be noted that the engagement between modules 12a and 12b can be made more substantial by the engagement of locking mechanism 28 on module 12a with the locking mechanism 30 on module 12b. It will be appreciated that the locking mechanisms 28 and 30, as well as their operation, can be of any type well known in the pertinent art.

Figure 4:
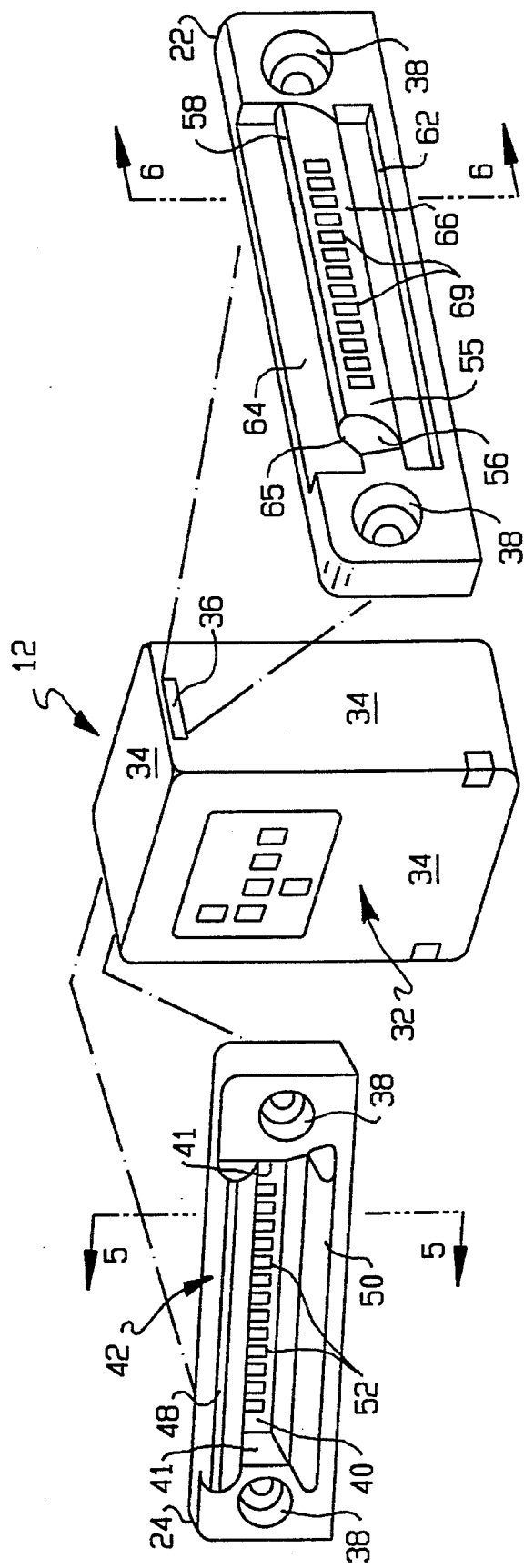
FIG. 4 is an exploded perspective view of a single module showing the interconnector parts of the present invention enlarged and out of scale.

As shown in FIG. 4, exemplary module 12 includes casing 32 which comprises walls 34 that surround and form a housing for internal electrical components (indicated as components 26 in FIG. 3). Module 12 also includes two connector portions according to the present invention: male connector portion 22 and female connector portion 24, as described above. Connector portions 22 and 24 may be made of plastics or other nonconductive materials, such as a glass filled thermoplastic polyester, by known processes such as molding or machining. The connector portions are preferably received in mating holes 36 (only one shown) in walls 34 of casing 32 in order to permit access to and communication with electrical components 26. The connector portions may be fixedly attached, for example to walls 34 or an internal support structure within casing 32 by screws placed through holes 38 provided for that purpose. Other means of fixed attachment may be devised by persons skilled in the art without departing from the scope of the present invention.

Figure 5:
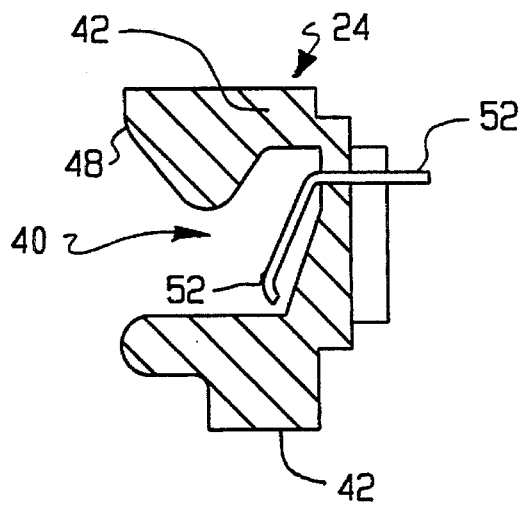
FIG. 5 is a cross-sectional view of a female connector portion according to the present invention, as taken through line 5—5 of FIG. 4.

As illustrated in FIG. 4, female connector portion 24 is located in a hole (not shown) through the wall 34 of casing 32 at a point where the dashed lines between female connector portion 24 and casing 32 intersect the casing. Referring to FIGS. 4 and 5, female connector portion 24 is formed with a substantially rectangular aperture 40. Aperture 40 is defined by a peripheral part 42 which surrounds aperture 40 and forms end walls 41 of aperture 40. Outward extending upper abutment 48 and lower abutment 50 further establish respective opposite portions of peripheral part 42. Screw holes 38, representing one possible means of attachment as described above, may be positioned in peripheral part 42.

A first set of one or more electrical contacts 52 is positioned within aperture 40 to form a preferably resilient contact surface therein. Electrical contacts 52 provide for electrical communication with electronic components 26 in casing 32 through female connector portion 24. For purposes of the present invention, electrical contacts 52 can be of any type well known in the pertinent art suitable for use as described herein. One type of electrical contact suitable for use in IV administration systems are stamped, formed beryllium copper contacts. Electrical contacts 52 are preferably biased against the mating contacts of male connector portion 22, as explained below.

Figure 6:
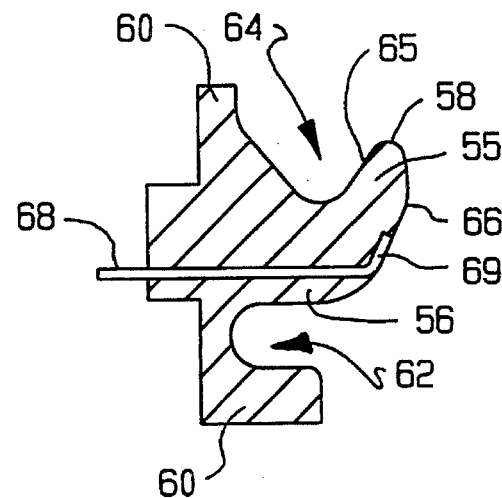
FIG. 6 is a cross-sectional view of a male connector portion according to the invention, as taken through line 6—6 of FIG. 4.

Turning to FIGS. 4 and 6, it can be seen that the male connector portion 22 is formed with an outward and upward extension 55 which has a base 56 and terminates in a curved lip 58. More specifically, curved lip 58 is angled upward to give extension 55 a hook-like shape. Base 56 of extension 55, together with peripheral part 60, define therebetween inwardly directed lower recess 62. An upper, upward opening recess 64 is defined on three sides generally by extension 55, base 56 and peripheral part 60. More specifically, curved lip 58 of extension 55 has a surface 65 which partially defines upper recess 60, and a surface 66 which faces substantially outwardly and away from casing 32 when the connector portion is placed thereon.

Male connector portion 22 has a second set of electrical contacts 68 passing therethrough and embedded into surface 66 of extension 55 to form an exposed contact surface 69. When male connector portion 22 is affixed to casing 32, the second set of electrical contacts 68 continue through hole 36 to communicate with electronic components 26 which are held within casing 32. Accordingly, electrical contact can be established with electronic components 26 through the second set of electrical contacts 68.

In the operation of the present invention, a module 12, such as module 12a, is positioned relative to another module 12, such as module 12b, substantially as shown in FIG. 2. Preferably, each module is provided with both male connector portion 22 and female connector portion 24 on opposite sides so that a multiplicity of modules may be interconnected. However, if only two modules were to be interconnected it would be sufficient to provide one with only female connector portion 24 and the other with only male connector portion 22. With the modules positioned as shown in FIG. 2, extension 55 (FIG. 6) of male connector portion 22 on module 12b is poised for insertion into aperture 40 (FIG. 5) of female connector portion 24 on module 12a. A subsequent rotation of the module 12a in the direction of arrow 25 will then cause curved lip 58 on the connector of module 12b to be inserted through the aperture 40 in female connector portion 24 of module 12a. (Alternatively, module 12b could be rotated opposite arrow 25.) This insertion positions the second set of electrical contacts 68 on male connector portion 22 of module 12b in electrical contact with the first set of electrical contacts 52 on female connector portion 24 of module 12a. Consequently, electronic components 26 in the two modules are placed in electrical communication as illustrated in FIG. 7.

In addition to the electrical connections, which are established between electrical contacts 52 and 68, the engagement of male connector portion 22 with female connector portion 24 as described above also structurally joins the two modules 12a, 12b together. As shown in FIG. 7, with the insertion of curved lip 58 through aperture 40, upper abutment 48 of female connector portion 24 is positioned in upper recess 64 of male connector portion 22 to vertically support the female connector portion by the male connector portion. Also, upper abutment 48 of female connector portion 24 is positioned behind angled lip 58 which prevents the connector portions from being laterally separated away from each other. Extension 55 being received in aperture 40 and abutting against end walls 41 also prevent the connector portions from being laterally separated in a side to side direction.

Additionally, lower abutment 50 of the female connector portion is matingly engaged in lower recess 62. It is this engagement which permits female connector portion 24 to vertically support male connector portion 22 by the upper surface of abutment 50 supporting base 56. Male connector portion 22 is thereby joined with female connector portion 24 to structurally engage modules 12a and 12b such that either module may support the weight of the other. Only rotation of one of the modules opposite that described above for engagement, and counter to the force of gravity, permits disengagement. It will be readily appreciated that multiple connector portions may be used to connect more than two modules as shown in FIGS. 1–4 and that other combinations and/or orientations may be employed, such as side and back connectors.

Figure 7:
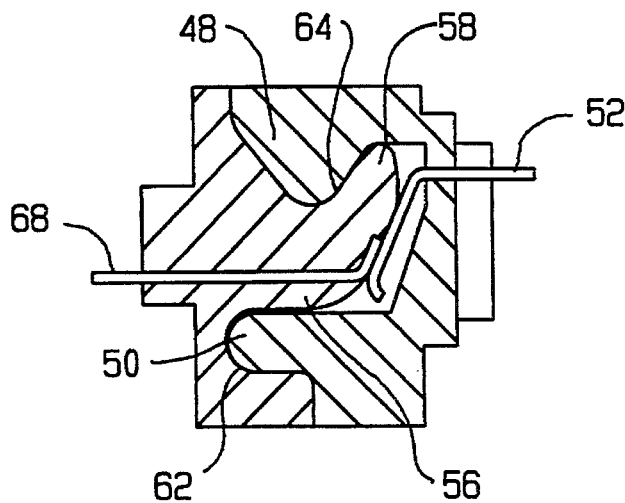
FIG. 7 is a cross-sectional view of a combined connector according to the present invention.

It also can be seen in FIG. 7 that the length of extension 55 is not as great as the depth of aperture 40. Thus, when the connector portions are combined, a void 72 is defined. The respective length and depth of the parts, as well as the position of contact 52 within aperture 40 are selected such that contact 52 is only resiliently deformed when the male connector portion is inserted. In this way continued positive electrical connections are assured after multiple uses.

While the particular connector as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. An electrical and structural interconnector, comprising:

a first part having a body portion with a hook-shaped portion extending in a direction outward and upward from the body portion and terminating along an upturned edge to define an upwardly opening recess between said edge and the first part body portion, said body portion defining an inwardly directed recess under said first part extending portion;

at least one electrical conductor extending through said first part and terminating in a contact surface on an outer surface of said extending portion;

a detachable second part having a body portion with a main body recess defined by an upper wall having a downward directed portion and a lower wall including an extension of said second part body portion, wherein said main body recess is configured and dimensioned to slidingly receive said first part extending portion when rotated into said recess in the outward and upward direction with said downward directed portion engaged in said first part upward opening recess and said second part extension received in said first part inwardly directed recess such that contact between said portions secures said first part against movement in lateral or vertical directions with respect to the second part; and at least one electrical conductor extending through said second part and terminating in a contact surface positioned within said main body recess to be contacted by said first part contact surface and resiliently deformed by said first part extending portion when received in said recess to provide an electrical connection between said conductors.

2. The interconnector according to claim 1, wherein:

the first part extending portion extends outward from the first part body portion by a first predetermined distance; and the second part main body recess has a depth greater than said first predetermined distance, such that when the first part is received in the second part a void is defined between the first part extending portion and the second part body portion, wherein said second part contact surface resiliently deforms into said void when in contact with the first part contact surface.

* * * * *